United States Patent
Schlichte

(10) Patent No.: US 7,603,887 B2
(45) Date of Patent: Oct. 20, 2009

(54) BREATH ALCOHOL-MEASURING DEVICE, PROCESS AND SYSTEM

(75) Inventor: Mladen Schlichte, Luebeck (DE)

(73) Assignee: Dräger Medical AG & Co. KG, Lübeck (DE)

(*) Notice: Subject to any disclaimer, the term of this patent is extended or adjusted under 35 U.S.C. 154(b) by 238 days.

(21) Appl. No.: 11/733,813

(22) Filed: Apr. 11, 2007

(65) Prior Publication Data

US 2007/0266766 A1    Nov. 22, 2007

(30) Foreign Application Priority Data

May 20, 2006    (DE) .................. 10 2006 023 837

(51) Int. Cl.
*G01N 1/22* (2006.01)
*A61B 5/085* (2006.01)
*A61B 5/097* (2006.01)

(52) U.S. Cl. .................. 73/23.3; 600/533; 600/532

(58) Field of Classification Search .................. 73/23.3; 600/529–543
See application file for complete search history.

(56) References Cited

U.S. PATENT DOCUMENTS

| 4,051,843 A | 10/1977 | Franetzki et al. |
| 4,082,088 A * | 4/1978 | Franetzki et al. ............ 600/533 |
| 4,809,810 A | 3/1989 | Elfman et al. |
| 5,734,090 A | 3/1998 | Koppel et al. |

FOREIGN PATENT DOCUMENTS

| DE | 20 45 403 C3 | 3/1972 |
| DE | 24 14 019 C3 | 9/1975 |
| DE | 25 08 319 C3 | 9/1976 |
| DE | 25 41 729 C2 | 11/1976 |
| DE | 26 31 470 C3 | 1/1978 |
| DE | 28 42 596 C2 | 12/1979 |
| DE | 270 007 | 7/1989 |
| GB | 1 500 627 | 2/1978 |
| GB | 1 521 412 | 8/1978 |

OTHER PUBLICATIONS

M. P. Hlastala. "Breathing-related limitations to the alcohol breath test." DWI Journal: Science and Law 17:1-4. Dec. 2002.*

* cited by examiner

*Primary Examiner*—Lisa M Caputo
*Assistant Examiner*—Punam Patel
(74) *Attorney, Agent, or Firm*—McGlew and Tuttle, P.C.

(57) ABSTRACT

A device, a system and a process is provided for the use of a breath alcohol-measuring device (1) with improved personal identification. The breath alcohol-measuring device (1) is combined with a pulse oscillometer (4) such that the initially measured values of the complex airway resistance of a test subject are stored in an evaluating and control unit (3) connected to the breath alcohol-measuring device (1) and to the pulse oscillometer (4) and compared to subsequently measured values of a test subject. A breath alcohol measurement is released and/or a vehicle immobilizer (2) is actuated in case of agreement of stored values with subsequently measured values.

10 Claims, 1 Drawing Sheet

BREATH ALCOHOL-MEASURING DEVICE, PROCESS AND SYSTEM

CROSS REFERENCE TO RELATED APPLICATIONS

This application claims the benefit of priority under 35 U.S.C. § 119 of German Patent Application DE 10 2006 023 837.0 filed May 20, 2006, the entire contents of which are incorporated herein by reference.

FIELD OF THE INVENTION

The present invention pertains to a process and a device for the use of a breath alcohol-measuring device.

BACKGROUND OF THE INVENTION

Breath alcohol-measuring devices are known to be used in the area of traffic checks by the police or also to test employees within companies in order to check alcohol abuse and especially to eliminate work-related or industrial accidents due to the influence of alcohol. The principle of measurement has proved itself and is based, in general, on an electrochemical measurement or on the measurement of the infrared optical absorption.

In addition, there have been so-called Interlock® devices for some years now, i.e., vehicle immobilizers especially in motor vehicles, which are combined with a breath alcohol-measuring device. These are used to prevent a driver who is under the influence of alcohol from starting up the motor vehicle in question.

The risk of manipulation is a problem in the case of the prior-art combinations of vehicle immobilizers and breath alcohol-measuring devices because the breath samples for the breath alcohol measurement may be given by persons other than the authorized driver.

SUMMARY OF THE INVENTION

Therefore, there is a need for a technical solution for personal identification during the use of a breath alcohol-measuring device. This is especially so with breath alcohol-measuring device in combination with a vehicle immobilizer.

According to the invention, a process is provided for using a breath alcohol-measuring device with personal identification, the process includes combining a breath alcohol-measuring device with a pulse oscillometer and performing an initial measurement of the airway resistance of a test subject at first by means of the pulse oscillometer. The measurement values of the test subject are stored. The stored values are compared to the currently measured values during each subsequent breath alcohol measurement. A subsequent breath alcohol measurement is released or accepted only if the currently measured values agree with the stored values.

The evaluation of the measured values may advantageously be carried out in a frequency-dependent manner for pressure and flow measured values.

Pressure surges generated by means of the pulse oscillometer may advantageously have a frequency in the range of 1 Hz to 50 Hz.

A vehicle immobilizer may advantageously be actuated as a function of the result of the breath alcohol measurement.

According to a further aspect of the invention, a device is provided for carrying out a process for breath alcohol measurement. The device includes a breath alcohol-measuring device combined with a pulse oscillometer such that the initially measured values of the complex airway resistance of a test subject are stored in an evaluating and control unit connected to the breath alcohol-measuring device and to the pulse oscillometer. The evaluating and control unit compares subsequently measured values of a test subject with stored values. A breath alcohol measurement is released/accepted and/or a vehicle immobilizer is actuated in case of agreement between stored values and subsequently measured values.

The breath alcohol-measuring device and the pulse oscillometer may advantageously be embodied in one assembly unit.

The breath alcohol-measuring device may advantageously be connected to an immobilizer of a vehicle.

The essential advantage of this process and this device and system is that the risk of manipulation by externally influencing the measurement process is practically ruled out.

An exemplary embodiment will be explained below by means of a single FIGURE. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
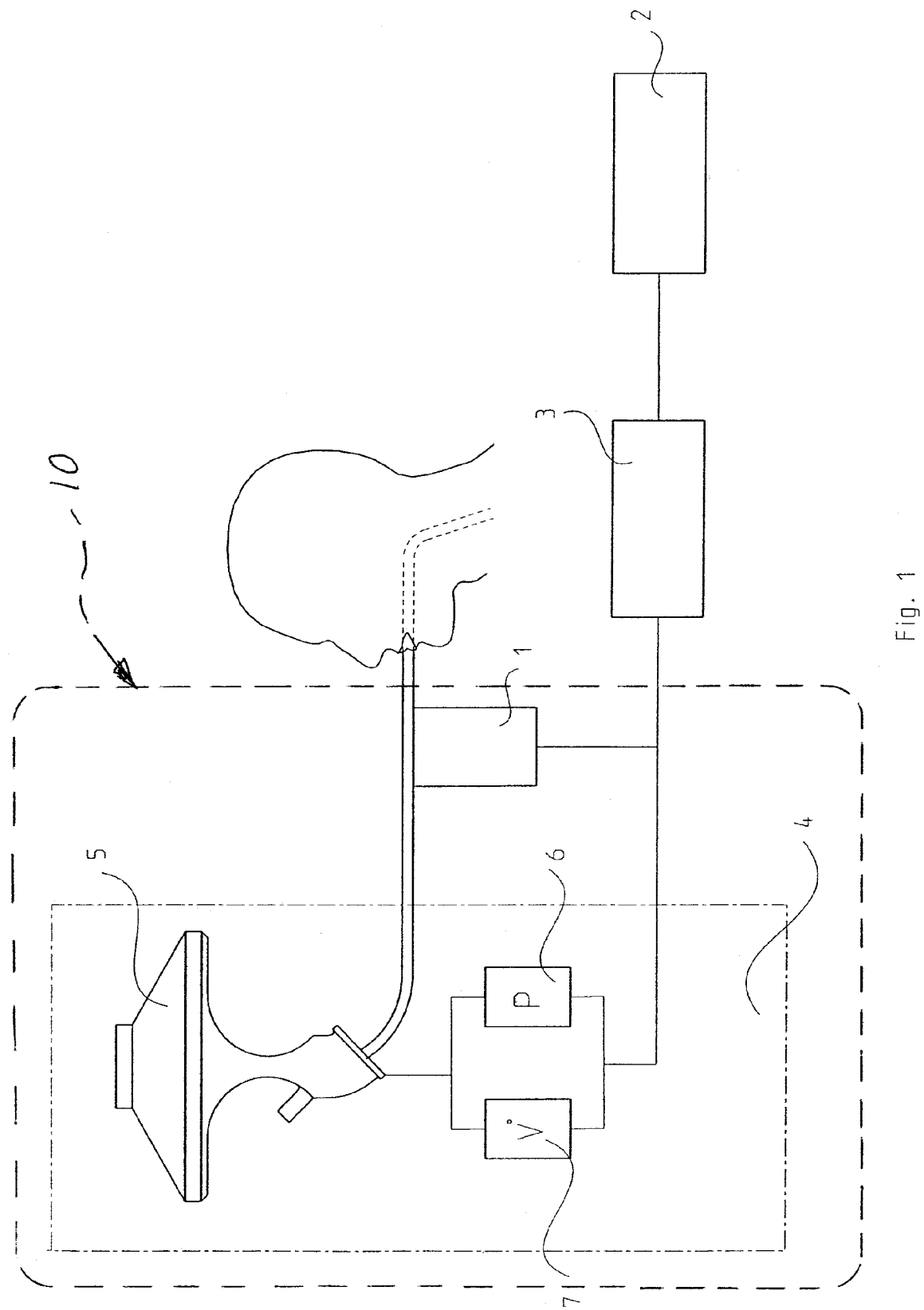
FIG. 1 is a schematic view showing the most important components of a device and system with a breath alcohol-measuring device.

Referring to the drawings in particular, the breath alcohol-measuring device/system of the invention is shown in FIG. 1. The breath alcohol-measuring device/system includes a breath alcohol-measuring device 1, a vehicle immobilizer (system shutoff/lock) 2, an evaluating and control unit 3, as well as a pulse oscillometer 4. The breath alcohol-measuring device 1 and the pulse oscillometer 4 may be embodied in one assembly unit generally designated 10. A test subject is connected by a breathing tube to the breath alcohol-measuring device 1 and to the pulse oscillometer 4. The pulse oscillometer 4 includes an external pulse generator 5 (generating pulses with a loudspeaker membrane) as well as a pressure sensor 6 and a flow sensor 7. The pressure sensor 6 and the flow sensor 7 are operatively (electrically, wirelessly, etc.) connected to the control unit 3. The breath alcohol measuring device 1 is operatively (electrically, wirelessly, etc.) connected to the control unit 3. The control unit 3 is operatively (electrically, wirelessly, etc.) connected to the vehicle immobilizer 2.

The personal identification of the driver, who is also called the test subject, is carried out by means of the pulse oscillometer 4 in the same breath as for the expired sample. The breath alcohol measurement takes place in the breath alcohol-measuring device 1. The driver's complex airway resistance, comprising a real portion, which represents the flow resistance proper, and an imaginary portion, which represents a blind resistance characteristic of the particular person, is suitable for the identification of the driver based on the characteristic behavior depending on a pressure surge imposed on the respiratory system from the outside. The resulting pressure-flow signal measured is generated in pulse oscillometry by the external pulse generator 5 as part of the pulse oscillometer 4, for example, by a correspondingly actuated loudspeaker membrane. The characteristic response of the particular, person-specific respiratory system is thereupon measured. The complex airway resistance of the particular driver or test subject is determined in a separate initial measurement and measured for each subsequent breath sample and compared to characteristic values stored in the evaluating and control unit 3. The vehicle immobilizer 2 is released in case of identity of the values.

The test subject, whose complex airway resistance is to be determined, breathes breathing air, for example, via a Y-piece with pressure and flow sensor 6, 7. The sensors record the signals of the total pressure and total flow, comprising a component that goes back to the spontaneous respiration and the superimposed pulse signal. The connected evaluating and control unit 3 separates the pulse signals from the respiration by a time and frequency analysis, especially a Fourier analysis.

The breath alcohol-measuring device 1 is preferably combined with the pulse oscillometer 4 in one assembly unit 10.

The breath alcohol-measuring device 1 contains, for example, an electrochemical measuring cell or an infrared optical measuring arrangement.

While a specific embodiment of the invention has been shown and described in detail to illustrate the application of the principles of the invention, it will be understood that the invention may be embodied otherwise without departing from such principles.

What is claimed is:

1. A breath alcohol-measuring process, comprising the steps of:
    providing a breath alcohol-measuring device;
    providing a pulse oscillometer;
    operating the pulse oscillometer in combination with the breath alcohol-measuring device such that an initial measurement of the complex airway resistance of a test subject is performed by means of the pulse oscillometer and measurement values of the initial measurement of the complex airway resistance of the test subject are stored as stored values;
    subsequent to the step of operating the pulse oscillometer in combination with the breath alcohol-measuring device, again operating the pulse oscillometer in combination with the breath alcohol-measuring device to provide a current breath alcohol measurement and current complex airway resistance measured values;
    comparing the stored values to the current complex airway resistance measured values; and
    releasing or accepting the current breath alcohol measurement only if the the current complex airway resistance measured values agree with the stored values.

2. A process in accordance with claim 1, wherein comparing the stored values includes an evaluation of measured pressure and flow values of the test subject carried out in a frequency-dependent manner.

3. A process in accordance with claim 1, wherein pressure surges generated by means of said pulse oscillometer have a frequency in the range of 1 Hz to 50 Hz.

4. A process in accordance with claim 1, further comprising providing a vehicle immobilizer and actuating the vehicle immobilizer as a function of the result of the breath alcohol measurement.

5. A device for breath alcohol-measuring, the device comprising:
    a breath alcohol-measuring device for providing a breath alcohol measurement;
    a pulse oscillometer for providing initially measured values of the complex airway resistance of a test subject and providing subsequently measured values of the complex airway resistance;
    an evaluating and control unit connected to said breath alcohol-measuring device and connected to said pulse oscillometer, said evaluating and control unit comparing said initially measured values to said subsequently measured values and releasing or accepting a breath alcohol measurement; and
    a vehicle immobilizer connected to said evaluating and control unit, said vehicle immobilizer being released and/or actuated based on a breath alcohol measurement in the case of agreement between said initially measured values and subsequently measured values.

6. A device in accordance with claim 5, wherein said breath alcohol-measuring device and said pulse oscillometer are embodied in one assembly unit.

7. A breath alcohol-measuring system comprising:
    a breath alcohol-measuring device for providing a breath alcohol measurement of a test subject via a breathing tube;
    a pulse oscillometer with a pulse generator generating pulses and a pressure sensor and a flow sensor, said pulse oscillometer imposing a pressure surge on a respiratory system of a test subject via the breathing tube and sensing a complex airway resistance of the test subject with the pressure sensor and a flow sensor for providing initially measured values of the complex airway resistance of a test subject and providing subsequently measured values of the complex airway resistance;
    an evaluating and control unit connected to said breath alcohol-measuring device and connected to said pulse oscillometer, said evaluating and control unit providing test subject personal identification based on a comparison of one or more of said initially measured values with one or more of said subsequently measured values.

8. A device according to claim 7, wherein based on test subject personal identification or inability to provide test subject personal identification, said evaluating and control unit releases or accepts a breath alcohol measurement.

9. A device according to claim 8, further comprising:
    a vehicle immobilizer connected to said evaluating and control unit, said vehicle immobilizer being released and/or actuated based on a breath alcohol measurement in the case of agreement between stored values and subsequently measured values.

10. A system in accordance with claim 9, wherein said breath alcohol-measuring device and said pulse oscillometer are embodied in one assembly unit.

* * * * *